(12) United States Patent
Arican et al.

(10) Patent No.: US 10,058,715 B2
(45) Date of Patent: Aug. 28, 2018

(54) METHOD AND DEVICE FOR QUALITY ASSURANCE OF A RADIATION THERAPY APPARATUS

(71) Applicant: Ion Beam Applications, Louvain-la-Neuve (BE)

(72) Inventors: Salih Arican, Poxdorf (DE); Juan Carlos Celi, Heidelberg (DE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 15/328,668

(22) PCT Filed: Jul. 15, 2015

(86) PCT No.: PCT/EP2015/066111
§ 371 (c)(1),
(2) Date: Jan. 24, 2017

(87) PCT Pub. No.: WO2016/008901
PCT Pub. Date: Jan. 21, 2016

(65) Prior Publication Data
US 2017/0165505 A1 Jun. 15, 2017

(30) Foreign Application Priority Data
Jul. 15, 2014 (EP) .................................... 14177122

(51) Int. Cl.
*A61N 5/10* (2006.01)
(52) U.S. Cl.
CPC .......... *A61N 5/1075* (2013.01); *A61N 5/1048* (2013.01); *A61N 2005/1076* (2013.01)
(58) Field of Classification Search
CPC ................ A61N 5/1048; A61N 5/1075; A61N 2005/1076
See application file for complete search history.

(56) References Cited

U.S. PATENT DOCUMENTS

| 2013/0123565 A1* | 5/2013 | Denis ................... A61N 5/1075 600/1 |
| 2014/0073834 A1 | 3/2014 | Hildreth |
| 2015/0352376 A1* | 12/2015 | Wiggers ............... A61N 5/1075 250/252.1 |

FOREIGN PATENT DOCUMENTS

WO    WO 2011/011471 A1    1/2011

OTHER PUBLICATIONS

"David—a translucent multi-wire transmission ionization chamber for in vivo verification of IMRT and conformal irradiation techniques," B. Poppe et al., Phys. Med. Biol., vol. 51, No. 5, pp. 1237-1246, Feb. 15, 2006.

(Continued)

*Primary Examiner* — Mark R Gaworecki
(74) *Attorney, Agent, or Firm* — Finnegan, Henderson, Farabow, Garrett & Dunner LLP

(57) ABSTRACT

The invention relates to a method for quality assurance of a radiation field (30) emitted by a radiation therapy apparatus (10), comprising the steps of: (i) providing an ionization chamber (40) detector as reference detector for measuring the dose of the radiation field (30) at the exit of the radiation head (20), said ionization chamber (40) having a size and being positioned for being traversed by said radiation beam (30), said ionization chamber (40) having an attenuation equivalent to less than 1 mm Al; (ii) providing one or more field detectors (50); moving the field detector (50) across the radiation field (30) and measuring simultaneously the dose from the field detector (50) and from the ionization chamber (40); (iii) computing the ratio of the dose from the field detector (50) to the dose of the ionization chamber (40). The invention also relates to a device for performing the method.

20 Claims, 1 Drawing Sheet

(56) References Cited

OTHER PUBLICATIONS

PTW, "Small Field Dosimetry Application Guide," 36 pages, retrieved on Jan. 23, 2017 from http://connect.physicsworld.com/Journals//2014/12/19/PTW_Small_Field_Application_Guide_Note_en_92020000_04.pdf, Sep. 9, 2013.
European Search Report dated Nov. 9, 2015, 3 pages.
Kapsch, R-P. et al. (2009). "On the performance of monitor chambers to measure the output of medical linear accelerators for high-precision dosimetric investigations," *WC 2009, IFMBE Proceedings* 25/I; pp. 85-88.

* cited by examiner

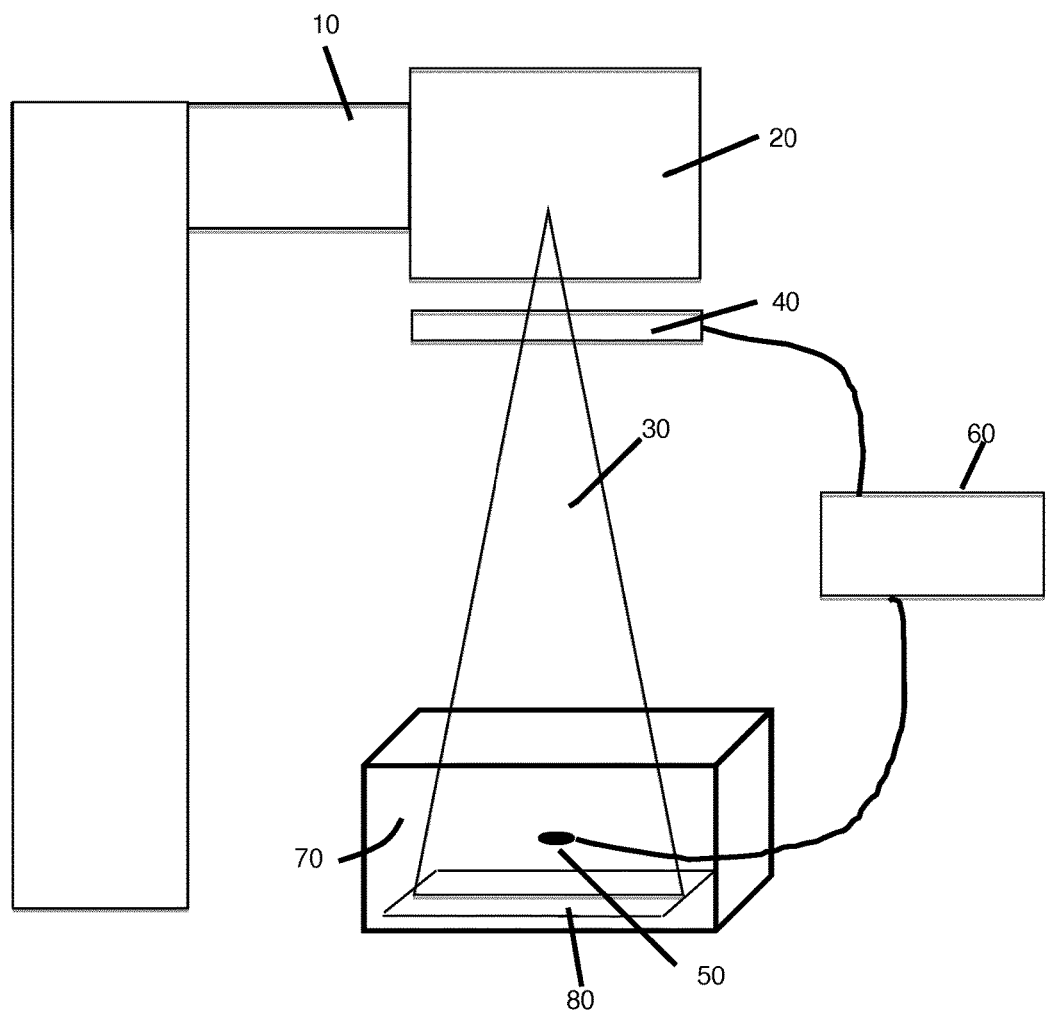

METHOD AND DEVICE FOR QUALITY ASSURANCE OF A RADIATION THERAPY APPARATUS

This is a National Phase Application which claims benefit to PCT Application No. PCT/EP/2015/066111 filed Jul. 15, 2015, which claims benefit of European Application No. 14177122.0 filed Jul. 15, 2014, all of which are incorporated herein by reference.

TECHNICAL FIELD

The present invention relates generally to the field of radiation therapy, and discloses a method and device for quality assurance of a radiation therapy apparatus. This method and device are especially applicable for the quality assurance of small fields.

DESCRIPTION OF RELATED ART

For performing the quality assurance of a photon beam emitted by a radiation therapy apparatus, it is known to use a water phantom. The beam is directed into the water contained in the water phantom. A small-size field detector such as diode or a small-size ionization chamber is moved across the volume of the water phantom, while measuring the dose. This can be performed in a continuous movement or step-by-step. As the intensity of the photon beam emitted by the radiation therapy apparatus may vary in time, it is necessary to use a reference detector measuring the intensity of the beam exiting the radiation therapy apparatus. This is performed by locating a reference dosimeter at the exit of the radiation therapy apparatus. It is common practice to locate the reference detector in a corner of the radiation field, so as not to disturb the measurements made by the field detector. By computing the ratio of the measurement of the field detector and of simultaneous measurement of the reference detector, it is possible to draw beam profiles or depth/dose curves that are independent of any fluctuations of the intensity of the beam. This method works well for conventional fields having sizes of typically 10 cm×10 cm at isocenter.

There is a growing interest for performing radiotherapy with small fields, eg. Fields as small as 1 cm×1 cm. Such small fields are used e.g. in stereotactic radiosurgery and in intensity modulated radiation therapy (IMRT). In the following, it will be considered that a field is a small field, if it is smaller than 4 cm×4 cm. Publication "J. U. Wuerfel, Dose measurements in small fields, Medical Physics International 1 (2013), 81" discusses the difficulties of dose measurements in small fields: "When measuring profiles, PDD curves, or TPR data, it is common practice to place a reference detector in the corner of the radiation field to correct for fluctuations of the linac output. In small fields there is not enough space to place such a reference detector inside the field." (end of page 83 of said document).

The possible solutions to this problem are also discussed:
- Using the monitor chamber of the linac as a reference detector. Besides the fact that this signal is usually not accessible, it should be noted that using this signal could not lead to a machine-independent quality assurance. These monitor chambers are usually positioned between the flattening filter or scattering foil and the photon beam secondary collimators. As such they don't measure the same beam as the field detector.
- Measure without reference detector. Relies on a stable linac.
- Use a reference detector outside the field: very weak signal, and therefore high noise. The measurement of such reference detector is very sensitive to the position. In case different field sizes must be tested, it is necessary to reposition the reference detector at the edge of the field for each different size, and therefore it is necessary to enter the treatment room.
- Irradiating a fixed number of MUs at each detector position. This is time consuming.

A "System and Method for Radiation Beam Measurement Normalization" is known from document US2014/0073834. This document discloses a system and method where a reference detector is positioned outside of the radiation beam but still exposed to head scatter. The reference detector may be positioned for instance on the top of the head of the radiotherapy apparatus. However, positioning such reference detectors may not be practical. Moreover, it has been experienced that the quality of scatter radiation on top of the radiation therapy apparatus is not good and reproducible enough for use as a reference signal. This document also discusses a prior art system wherein the reference detector is located in the radiation beam. However, this reference detector 120 of FIG. 3 is traversed by only a fraction of the radiation beam 124. Therefore, it may be necessary to reposition the reference detector as the beam size changes. Also, this reference detector may be sensitive to fluctuations in beam shape during scanning.

PRIOR ART DISCUSSION

The present invention aims at providing a device that overcomes the above-discussed drawbacks of the prior art.

In particular, it is an object of the present invention to provide a method and device for quality assurance of a radiation field emitted by a radiation therapy apparatus, which is adapted for measuring small radiation fields.

SUMMARY OF THE INVENTION

According to a first aspect, the invention is related to a method for quality assurance of a radiation field produced by a radiation therapy apparatus, said radiation therapy apparatus having a radiation head, and emitting a radiation beam, comprising the steps of: (i) providing an ionization chamber detector as reference detector for measuring a signal indicative of the dose of said radiation field at the exit of said radiation head, said ionization chamber having a size and being positioned for being traversed by said radiation beam; (ii) providing one or more field detectors; (iii) moving the field detector across the radiation field and measuring simultaneously the dose from the field detector and from the ionization chamber; (iv) computing the ratio of the dose from the field detector to the dose of the ionization chamber. The ionization chamber size and position are selected such that it is traversed by substantially all of said radiation beam. The method of the invention may also be used for commissioning a radiation therapy apparatus. The signal indicative of the dose may be the total dose or kerma of the radiation beam.

Preferably said ionization chamber has an attenuation equivalent to less than 1 mm Al or even preferably less than 0.5 mm Al.

In a preferred embodiment, the movement of the field detector may be a continuous movement, and said measuring is then performed continuously. This method is applicable when a motorized phantom is used.

Said moving may also comprise a succession of movements from one location to another one followed by a stay at said other location, and said measuring the comprises the integration of the measured doses during said stay. This is the step-by-step method.

The field detectors may be diodes having preferably a sensitive volume less that 0.3 mm3.

The field detectors may also be ionization chambers having preferably an attenuation less than equivalent to 0.5 mm Al;

The reference detector may be an ionization chamber having preferably an attenuation less than 2%.

The method may be used in a phantom, and said moving step is then performed in a phantom.

In another aspect, the invention is related to a device for quality assurance of a radiation field produced by a radiation therapy apparatus, said radiation therapy apparatus having a radiation head, and emitting a radiation beam, comprising: (i) an transmission ionization chamber detector as reference detector for measuring the dose of said radiation field at the exit of said radiation head, said ionization chamber having a size for being traversed by said radiation beam when positioned in said radiation beam; (ii) one or more field detectors; (iii) a control unit adapted for acquiring simultaneously the dose from the one or more field detectors and from the ionization chamber and for computing the ratio of the dose from the one or more field detectors to the dose of the ionization chamber.

Preferably said ionization chamber has an attenuation equivalent to less than 1 mm Al or even preferably less than 0.5 mm Al.

The one or more field detectors may be a single detector, but may also be a linear array of detectors a two-dimensional array of detectors. All the individual detectors have preferably a small size.

When the device is to be used with a water phantom, the control unit may advantageously be adapted for controlling the movements of the filed detector and to synchronize the acquisition with said movements.

BRIEF DESCRIPTION OF THE DRAWING

FIG. 1 is a schematic representation of an environment wherein the method and device of the invention may be used.

DETAILED DESCRIPTION OF THE INVENTION

FIG. 1 is a schematic representation of a radiation therapy apparatus 10, having a radiation head 20, and a device for quality assurance 40, 50, 60 according to the invention. The radiation therapy apparatus 10 may comprise a linac or waveguide for accelerating electrons to an energy in the range of 4 MeV up to 40 MeV, and the radiation head 20 may comprise magnets for directing the electron beam, a target for generating high energy photons, and a collimation system for shaping a radiation beam 30. According to the invention a device 40, 50, 60 for quality assurance of the radiation field 30 of the radiation therapy apparatus 10 is provided. This device for quality assurance comprises a reference detector 40, a field detector 50, and a control unit 60. As shown, the reference detector has a size, and is positioned in such a way that it intercepts and is traversed by the radiation beam 30. A field detector is positionable and moveable across the radiation field 80. In a preferred embodiment of the invention, the device and method is used together with a phantom, such as a water phantom 70. The field detector 50 may be positioned with high accuracy (better than 0.5 mm) within the water phantom.

When the step-by-step method is used, the field detector 50 is located at a know location, the beam is produced, and the acquisition of the dose from the field detector 50 and of the reference detector 40 are performed by the control unit 60. The ratio of these two measurements is performed by the control unit 60. This ratio will be insensitive to of any beam intensity variation or inaccuracy in the time period of acquisition, i.e. of integration of the charges produced during the irradiation. The field detector is then moved to another location, and the process is repeated. Based on the collected data, the beam profiles and depth/dose curves may be determined. When using an ionization chamber as a reference detector, especially an ionization chamber with a low attenuation, it is ensured that the beam spectrum is not changed, and thereby that the depth/dose curves are not shifted.

When a motorized water phantom is used, the continuous method (i.e. scanning mode) may be performed. The control unit 60 instructs the water phantom 70 to move the field detector 50 along a predetermined track, according to a predetermined speed. As an example, the control unit 60 performed an acquisition every 20 ms, while the field detector 50 was moved at 3 mm/s. For measuring a field of 10 mm, together with a penumbra region of 10 mm at both sides, a total of 500 measurement points are acquired in 10 s.

Suitable field detectors 50 may be the ionization chambers for Stereotactic/IMRT provided by IBA Dosimetry, reference CC01 or CC04 having an active volume of 0.01 cm$^3$ and 0.04 cm$^3$, an Inner radius of 1 and 2 mm and a sensitivity of 317 (Gy/C×10$^7$) 94 (Gy/C×10$^7$) respectively. Diodes may also be used, such as the IBA diode SFD, designed for stereotactic and IMRT, and having a diameter of the active area 0.6 mm, a thickness of the active volume 0.06 mm, and a sensitivity of 17 (Gy/C×10$^7$). Preferably, the field detectors according to the method and device of the invention have an active area equal or smaller than 0.5 cm2, more preferably an active area equal or smaller than 0.3 cm2. In order to obtain even faster results, a linear diode array may be used.

Suitable reference detectors 40 may be the Kermax circular or rectangular ionization chamber provided by IBA Dosimetry. The circular chamber has a sensitive region having a diameter of 92 mm. The rectangular version has a sensitive area of 146 mm×146 mm, and a sensitive volume of 240 cm$^3$. It has been determined that these detectors, with a beam 6 MeV photons, and a electrode voltage of −420 V will produce an attenuation of less than 2%. Such a high transparency is not essential, but advantageous. The invention will work with less transparent reference detectors, for example detectors having a attenuation up to 5% or even up to 10%, although secondary radiation might reach the field detector and perturb the measurement. The inventors have found that in order to reduce scattering effects, the transmission ionization chamber preferably should have a thickness smaller than 1 mm of aluminum equivalent. More preferably, the transmission ionization chamber should have a thickness smaller than 0.5 mm aluminum equivalent. Such reference detectors are capable of measuring area kerma product (AKP), sometimes known as dose area product or AEP (Area Exposure Product). It is known that such measurements are independent of the precise position of the detector in the beam, provided it intercepts the whole extent of the beam. Using such a reference detector, the quality assurance of large (10 cm×10 cm) fields as well as small (less than 4 cm×4 cm) may be performed in a reliable and time saving way. It has been determined that by using a reference detector 40, such as the above examples, having a sensitive area larger than 50 cm², and locating the reference detector 40 between the radiation head 20 and the radiation field 80, at a position such that all of the beam 30 is traversed by the detector, all field sizes, large and small, occurring in clinical practice could be measured. The device of the invention may optionally also comprise a mechanical holder for maintaining the reference detector at the exit of the radiation head or at a distance of the radiation head. Being positioned at a fixed position at the exit of the radiation head, the reference detector provides a reproducible measurement, independent of other operating conditions of the apparatus. The reference detectors used have an optical transparency better than 70%. This is an advantage in that it facilitates the alignment of the field detector in a light beam emitted from the radiation head.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated. As a consequence, all modifications and alterations will occur to others upon reading and understanding the previous description of the invention. In particular, dimensions, materials, and other parameters, given in the above description may vary depending on the needs of the application.

The invention claimed is:

1. A method for quality assurance of a radiation field produced by a radiation therapy apparatus, said radiation therapy apparatus having a radiation head and emitting a radiation beam, the method comprising:
   providing a transmission ionization chamber detector as a reference detector for measuring a signal indicative of the dose of said radiation beam at the exit of said radiation head, an ionization chamber of said ionization chamber detector having a size and being positioned for being traversed by said radiation beam;
   providing one or more field detectors;
   positioning the one or more field detectors in the radiation field;
   moving said one or more field detectors in a continuous movement;
   continuously measuring simultaneously the dose from the one or more field detectors and from the ionization chamber; and
   computing the ratio of the dose from the one or more field detectors to the dose from the ionization chamber.

2. The method according to claim 1, wherein said ionization chamber has an attenuation equivalent to less than 1 mm Al.

3. The method according to claim 1, further comprising:
   moving said one or more field detectors in a succession of movements from a first location to a second location followed by a stay at said second location, and
   wherein said measuring comprises integration of said signal during said stay.

4. The method according to claim 1, wherein said one or more field detectors comprise a diode having a sensitive volume less than 0.3 mm³.

5. The method according to claim 1, wherein said one or more field detectors comprise an ionization chamber having an attenuation less than equivalent to 0.5 mm Al.

6. The method according to claim 1, wherein said reference detector is an ionization chamber having an attenuation less than 2%.

7. The method according to claim 1, wherein moving said one or more field detectors is performed in a phantom.

8. A device for quality assurance of a radiation field produced by a radiation therapy apparatus, said radiation therapy apparatus having a radiation head and emitting a radiation beam, comprising:
   a transmission ionization chamber detector as a reference detector for measuring a signal indicative of the dose of said radiation beam at the exit of said radiation head, an ionization chamber of said ionization chamber detector having a size for being traversed by said radiation beam when positioned in said radiation field;
   one or more field detectors; and
   a control unit adapted to control movement of the one or more field detectors, simultaneously measure the dose from the one or more field detectors and from the ionization chamber and to compute the ratio of the dose from the one or more field detectors to the dose from the ionization chamber, and synchronize the measurement with the movement.

9. The device according to claim 8, wherein said ionization chamber has an attenuation equivalent to less than 1 mm Al.

10. The device according to claim 8, wherein said one or more field detectors comprise a linear array of detectors.

11. The device according to claim 8, wherein said one or more field detectors comprise a two-dimensional array of detectors.

12. The device of claim 8 further adapted for performing quality assurance of a field smaller than 4 cm by 4 cm.

13. A method for quality assurance of a radiation field produced by a radiation therapy apparatus, said radiation therapy apparatus having a radiation head and emitting a radiation beam, the method comprising:
   providing a transmission ionization chamber detector between a collimation system of the radiation head and the radiation field as a reference detector for measuring a signal indicative of the dose of said radiation beam at the exit of said radiation head, said reference detector intercepting the whole extent of the radiation beam, and an ionization chamber of said ionization chamber detector having a size and being positioned for being traversed by said radiation beam;
   providing one or more field detectors;
   positioning the one or more field detectors in the radiation field;
   measuring simultaneously the dose from the one or more field detectors and from the ionization chamber; and
   computing the ratio of the dose from the one or more field detectors to the dose from the ionization chamber.

14. The method according to claim 13, wherein said one or more field detectors comprise a diode having a sensitive volume less than 0.3 mm³.

15. The method according to claim 13, wherein said one or more field detectors comprise an ionization chamber having an attenuation less than equivalent to 0.5 mm Al.

16. The method according to claim 13, wherein said reference detector is an ionization chamber having an attenuation less than 2%.

17. A device for quality assurance of a radiation field produced by a radiation therapy apparatus, said radiation therapy apparatus having a radiation head and emitting a radiation beam, comprising:

a transmission ionization chamber detector between a collimation system of the radiation head and the radiation field as a reference detector for measuring a signal indicative of the dose of said radiation beam at the exit of said radiation head, said reference detector intercepting the whole extent of the radiation beam, and an ionization chamber of said ionization chamber detector having a size for being traversed by said radiation beam when positioned in said radiation field;

one or more field detectors; and a control unit adapted to simultaneously measure the dose from the one or more field detectors and from the ionization chamber and to compute the ratio of the dose from the one or more field detectors to the dose from the ionization chamber.

18. The device according to claim 17, wherein said ionization chamber has an attenuation equivalent to less than 1 mm Al.

19. The device according to claim 17, wherein said one or more field detectors comprise a linear array of detectors.

20. The device according to claim 17, wherein said one or more field detectors comprise a two-dimensional array of detectors.

* * * * *